United States Patent
Greter et al.

(10) Patent No.: US 6,921,379 B2
(45) Date of Patent: Jul. 26, 2005

(54) BREAST PUMP

(75) Inventors: Andy Greter, Steinhausen (CH); Beda Weber, Cham (CH)

(73) Assignee: Medela AG, Baar (CH)

( * ) Notice: Subject to any disclaimer, the term of this patent is extended or adjusted under 35 U.S.C. 154(b) by 0 days.

(21) Appl. No.: 10/250,497

(22) PCT Filed: Dec. 20, 2001

(86) PCT No.: PCT/CH01/00732
§ 371 (c)(1),
(2), (4) Date: Oct. 17, 2003

(87) PCT Pub. No.: WO02/053208
PCT Pub. Date: Jul. 11, 2002

(65) Prior Publication Data
US 2004/0215138 A1 Oct. 28, 2004

(30) Foreign Application Priority Data
Jan. 3, 2001 (EP) .............................................. 01100241

(51) Int. Cl.⁷ .............................. A61M 1/06; A01J 5/04; A61B 5/00; F04B 17/03
(52) U.S. Cl. ........................... 604/74; 604/75; 600/573; 417/415; 119/14.08
(58) Field of Search .............................. 604/70–78, 118; 600/573; 417/415, 182–198; 119/14.08, 14.41, 14.02, 14.47

(56) References Cited

U.S. PATENT DOCUMENTS

| | | | | |
|---|---|---|---|---|
| 4,280,445 A | * | 7/1981 | Phillips | 119/14.02 |
| 4,365,589 A | * | 12/1982 | Phillips et al. | 119/14.02 |
| 4,961,726 A | | 10/1990 | Richter | 604/74 |
| 5,954,690 A | * | 9/1999 | Larsson | 604/74 |

FOREIGN PATENT DOCUMENTS

| | | | | |
|---|---|---|---|---|
| DE | 39 16 699 A1 | | 5/1989 | A61M/1/06 |
| WO | WO 00/66195 | | 11/2000 | A61M/1/06 |

* cited by examiner

*Primary Examiner*—Nicholas D. Lucchesi
*Assistant Examiner*—Roz Maiorino
(74) *Attorney, Agent, or Firm*—Baniak Pine & Gannon

(57) ABSTRACT

The invention relates to a breast pump, which in addition to a drive motor (7), vacuum diaphragm pump (1) and programme-controlled electronics (4), comprises a vacuum chamber (12) with a separation diaphragm (13), which is connected between a pump intake conduit (9) and an extraction hood (11). The first chamber (14) is equipped with a device (16) for the negative or positive aeration of said chamber. Said device (16) is also programme-controlled by the electronics (4) during the normal continuous operation of the pump (1).

3 Claims, 3 Drawing Sheets

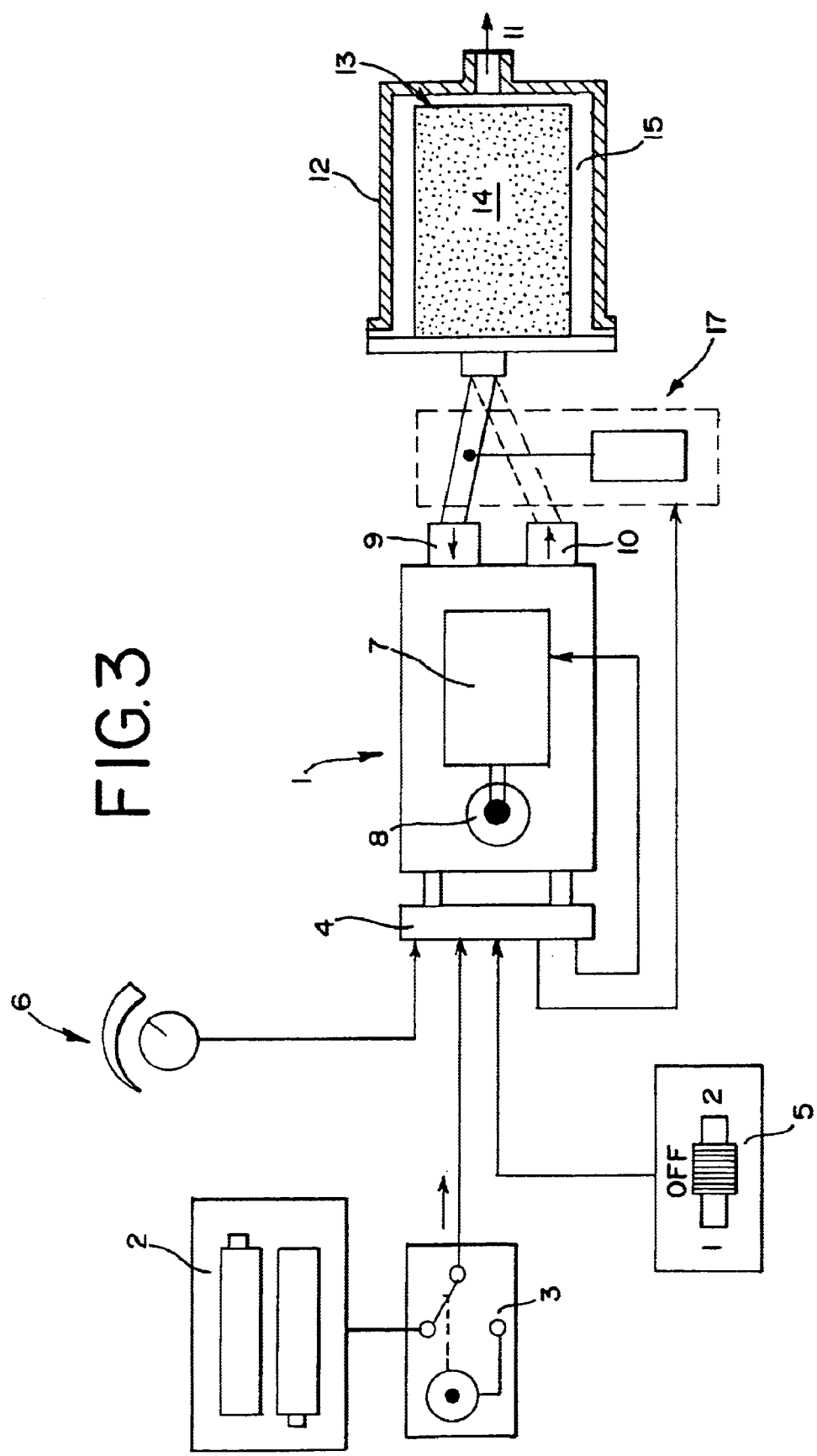

BREAST PUMP

The present invention relates to a breast pump with a diaphragm vacuum pump, drive motor and control electronics for setting the motor speed as a function of a preprogrammed vacuum profile, in particular a battery-operated breast pump.

Breast pumps are presently being developed which are operated according to a selectable program. At the start, a stimulation is generally provided which acts on the breast for a short period at reduced vacuum (e.g. 50–150 mmHg), but at a high frequency (e.g. 120 cycles/min), in order to stimulate the subsequent expression of milk.

The actual milk-pumping program runs at a higher vacuum (e.g. 100–250 mmHg) but with much fewer cycles (e.g. 40–80 cycles/min). A diaphragm pump is used as the vacuum pump. The desired vacuum is regulated by setting the speed of the drive motor of the pump. The program can also include a coasting phase at the end of suctioning (switching the vacuum back to, for example, 50–150 mmHg at, for example, 120–150 cycles/min).

A particularly advantageous suctioning program consists, in each cycle, of progressively building up the desired vacuum and holding the maximum vacuum for a predetermined time, then completely releasing the vacuum as quickly as possible (to zero vacuum) in order, after a predetermined rest period, to initiate the following cycle.

The object of the present invention is to provide a breast pump, of the type defined above, with means permitting the fastest possible vacuum release between the end of the "vacuum holding" and the "rest period at zero vacuum".

In the breast pump defined at the start, this object is achieved according to the invention by the features according to the characterizing part of claim 1.

Particular embodiments of the subject of the invention are defined in the dependent claims.

The subject of the invention is explained in greater detail below on the basis of illustrative embodiments shown in the drawings, where:

FIG. 3 shows a representation similar to FIG. 2, with an alternative of the controlled device for canceling the generated vacuum.

Figure 1:
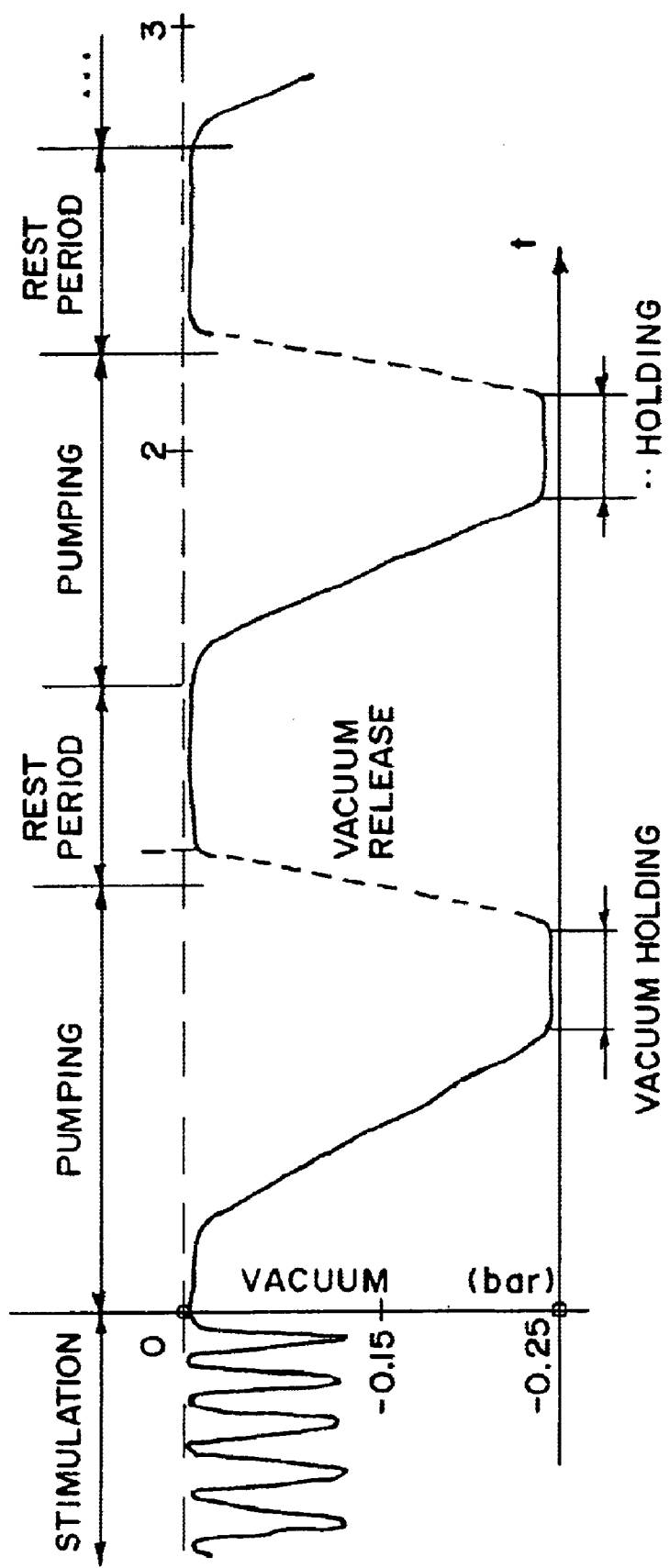
FIG. 1 shows a purely diagrammatic representation of the programmed vacuum profile of a breast pump.

FIG. 1 of the drawing shows diagrammatically the programmed profile of the vacuum during operation of a breast pump, where the actual pumping commences after possible stimulation at a vacuum of 50–150 mmHg at, for example, 120 cycles/min. The aim is to achieve a vacuum of 250 mmHg which is built up progressively from 0 to the end value, and which is maintained for a certain time per cycle and then released again as quickly as possible to 0. There, a brief rest period is interpolated before the next cycle is started (the actual pumping takes place at, for example, 40–80 cycles/min).

The desired vacuum is built up via electronic speed control of the electric motor for the vacuum pump (diaphragm pump). To reach a specified vacuum, the pump is driven at a predetermined speed which is retained during the pumping process. The vacuum release interpolated between the cycles and the subsequent rest period are effected not by changing the motor speed, but by vacuum release in a vacuum chamber, with separating diaphragm, coupled between pump and suction cap. The vacuum release takes place via a controlled device which as quickly as possible (without stopping the pump) releases the vacuum in the vacuum chamber by passive ventilation (valve to the environment) or by active pressure ventilation (pressure buildup in the vacuum chamber by connecting the ejection line of the vacuum pump).

By suitable setting of the motor speed of the pump drive, a desired profile of the vacuum can be set (programmed) during pumping, i.e. control of the cycles and of the desired maximum vacuum. The rest period can likewise be set by control of the device for canceling the built-up vacuum.

Figure 2:
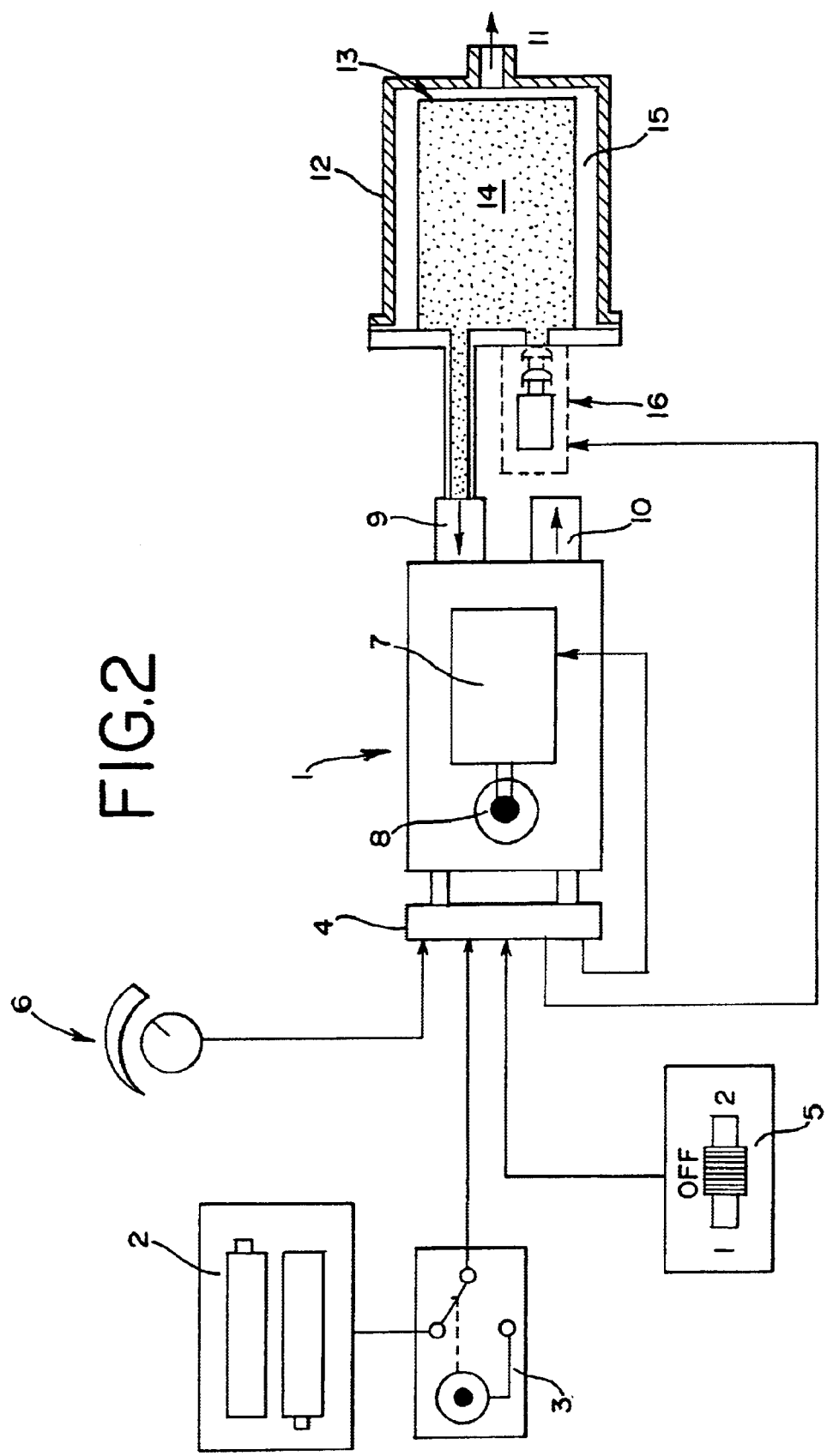
FIG. 2 shows the block diagram of a breast pump constructed according to the invention.

FIG. 2 of the drawing shows a purely diagrammatic representation of the construction of a battery-operated breast pump according to the invention.

The unit, i.e. the actual vacuum pump, is a diaphragm vacuum pump 1 known per se which is set in operation by batteries 2 via a main switch 3.

Control electronics 4 receive commands from a program for the desired curve profile during pumping (component 5), and commands for manual setting (component 6) (adjustment) of the vacuum and of the cycles, and act directly on the motor speed necessary for reaching the values.

The motor 7 drives a diaphragm pump via a crank mechanism 8, and the diaphragm pump generates a vacuum via the line 9 and ejects suctioned air via the line 10.

Because of its compact nature and its efficiency, the diaphragm vacuum pump used is in particular one which forms the subject matter of a patent application filed simultaneously by the Applicant.

A vacuum chamber 12 with separating diaphragm 13 is coupled between a suction cap hood 11 (not shown) and the vacuum pump 1 (unit). The first chamber 14 of the connected vacuum chamber 12 communicates with the suction line 9 of the pump 1, while the chamber 15 separated by means of the diaphragm 13 can be connected to the suction cap 11.

The first chamber 14 is equipped with a controlled valve 16 which, after opening, immediately releases the built-up vacuum (vacuum release in the pumping curve according to FIG. 1). The vacuum release is thus effected by passive ventilation of the first chamber of the vacuum chamber. (at the same time the vacuum in the second chamber and thus in the suction cap is also released).

The valve 16 is controlled, in accordance with the selected program, via the control electronics 4.

A variant of the breast pump according to FIG. 2 is shown, once again diagrammatically, in FIG. 3. The difference from the embodiment according to FIG. 2 lies in the device for canceling the vacuum built up in the vacuum chamber 12. Instead of the controlled valve 16 provided for passive ventilation, in this case a so-called valve switch 17 is provided which interrupts the connection between the suction line 9 and the first chamber 14 and connects the ejection line 10 of the pump to the chamber 14. In this way, the vacuum generated in the chamber 14 (and thus in the chamber 15 and the suction cap 11) is cancelled by positive pressure buildup. This is possible within a very short space of time because the pump continues to operate even during the vacuum release and the subsequent rest period. The command for switching the valve switch is likewise given via the programmed control electronics 4.

The central feature of the breast pump is, besides the advantageously miniaturized diaphragm pump, the vacuum chamber 12, also called the medium-separating chamber. By virtue of this chamber, the built-up vacuum can be canceled at any time (by program control) without interrupting the actual vacuum pump and can then be built up again without delay.

What is claimed is:

1. A breast pump, comprising: a diaphragm vacuum pump, drive motor control electronics for setting a motor speed of the vacuum pump as a function of a preprogrammed vacuum profile, a vacuum chamber coupled between the vacuum pump and a suction cap, the vacuum chamber including a separating diaphragm, a first chamber of the vacuum chamber communicating with a suction line of the vacuum pump, and a second chamber which can be connected to the suction cap, the first chamber being equipped with a controlled device for canceling a vacuum which has been built up.

2. The breast pump as claimed in claim 1, wherein the controlled device for canceling the vacuum in the vacuum chamber comprises a valve which is controlled by control electronics and which, when opened, connects the first chamber to atmosphere and passively removes air from the vacuum chamber.

3. The breast pump as claimed in claim 1, characterized in that the device for canceling the vacuum in the vacuum chamber consists of a valve switch which, when actuated, interrupts the suction line between the vacuum pump and the first chamber and connects said first chamber of the vacuum chamber to the ejection line of the vacuum pump building up a positive pressure, i.e. actively cancels the vacuum in the vacuum chamber by positive pressure buildup.

* * * * *